US012646623B2

(12) United States Patent　　　　(10) Patent No.:　US 12,646,623 B2
　　　Adiyoso et al.　　　　　　　　　(45) Date of Patent:　　　Jun. 2, 2026

(54) METHODS AND SYSTEMS FOR PROVIDING MOLECULAR DATA BASED ON CT IMAGES

(71) Applicant: Siemens Healthcare GmbH, Erlangen (DE)

(72) Inventors: Arnaud Arindra Adiyoso, Nuremberg (DE); Andre Aichert, Erlangen (DE); Marvin Teichmann, Erlangen (DE); Tobias Heimann, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 664 days.

(21) Appl. No.: 18/155,176

(22) Filed: Jan. 17, 2023

(65) Prior Publication Data

US 2023/0230704 A1　　Jul. 20, 2023

(30) Foreign Application Priority Data

Jan. 19, 2022　(EP) ..................................... 22152264

(51) Int. Cl.
　G16H 50/20　　　(2018.01)
　A61B 6/03　　　(2006.01)
　G06T 7/00　　　(2017.01)
(52) U.S. Cl.
　CPC .............. G16H 50/20 (2018.01); A61B 6/03 (2013.01); G06T 7/0012 (2013.01); G06T 2207/20084 (2013.01)
(58) Field of Classification Search
　CPC ........ G16H 50/20; G16H 30/40; G16H 30/20; A61B 6/03; A61B 6/032; A61B 6/50;
(Continued)

(56) References Cited

U.S. PATENT DOCUMENTS 11,741,604 B2 *　8/2023　Kapur ...................... G06T 7/11
　　　　　　　　　　　　　　　　　　　382/128
2022/0185858 A1　6/2022　Li et al.

FOREIGN PATENT DOCUMENTS

CN　　　110055224 A　　7/2019
CN　　　111553892 A　　8/2020
WO　WO 2021118918 A1　6/2021

OTHER PUBLICATIONS

Jiang Mengmend et al.; "Assessing PD-L1 Expression Level by Radiomic Features From PET/CT in Nonsmall Cell Lung Cancer Patients: An Initial Result", Mengmeng Jiang MD et al., Academic Radiology, vol. 27, No. 2, pp. 171-179.
(Continued)

*Primary Examiner* — Kent Yip
(74) *Attorney, Agent, or Firm* — Harness, Dickey & Pierce, P.L.C.

(57)　　　　　　ABSTRACT
One or more example embodiments of the present invention is based on a computer-implemented method for providing molecular data. The method comprises receiving a computed tomography image of at least a part of a lung of a patient, wherein the computed tomography image depicts at least one lung nodule. The molecular data is determined by processing first input data with a first trained function, wherein the first input data is based on the computed tomography image, and wherein the molecular data relates to a biomarker within at least one of a genome of the patient, a transcriptome of the patient, a proteome of the patient or a metabolome of the patient. Furthermore, the molecular data is provided. Providing the molecular data can comprise at least one of displaying, transmitting or storing the molecular data.

12 Claims, 6 Drawing Sheets

(58) Field of Classification Search
CPC ................ A61B 6/5211; G06T 7/0012; G06T
2207/20084; G06N 3/08; G16B 40/00
See application file for complete search history.

(56) References Cited

OTHER PUBLICATIONS

Zhang, Baihua et al: "Deep CNN Model Using CT Radiomics Feature Mapping Recognizes EGFR Gene Mutation Status of Lung Adenocarcinoma"; Frontiers in Oncology; Feb. 12, 2021 (Feb. 12, 2021), XP55932796.

Chen Y. et al.: "Prediction of EGFR mutations by conventional CT-features in advanced pulmonary adenocarcinoma," Eur. J. Radiol., vol. 112, No. Aug. 2018, pp. 44-51, 2019, doi: 10.1016/j.ejrad.2019.01.005.

Rossi G. et al.: "Radiomic Detection of EGFR Mutations in NSCLC," Cancer Res., vol. 81, No. 3, pp. 724-731, 2021, doi: 10.1158/0008-5472.CAN-20-0999.

Girshick et al., "Rich feature hierarchies for accurate object detection and semantic segmentation" ar-Xiv:1311.2524.

Nair J.K.R. et al.: "Radiogenomic Models Using Machine Learning Techniques to Predict EGFR Mutations in Non-Small Cell Lung Cancer" in Can Assoc Radiol J. Feb. 2021;72(1):109-119. doi: 10.1177/0846537119899526.

Mu W. et al.: "Non-invasive decision support for NSCLC treatment using PET/CT radiomics," Nat. Commun., vol. 11, No. 1, 2020, doi: 10.1038/s41467-020-19116-x.

Zhu .Y et al.: "A CT-derived deep neural network predicts for programmed death ligand-1 expression status in advanced lung adenocarcinomas," Ann. Transl. Med., vol. 8, No. 15, pp. 930-930, 2020, doi: 10.21037/atm-19-4690.

Zhang Y. et al.: "Improving prognostic performance in resectable pancreatic ductal adenocarcinoma using radiomics and deep learning features fusion in CT images," Sci. Rep., vol. 11, No. 1, pp. 1-12, 2021, doi: 10.1038/s41598-021-80998-y.

Zhang Y. et al.: "Simultaneous identification of EGFR, KRAS, ERBB2, and TP53 mutations in patients with non-small cell lung cancer by machine learning-derived three-dimensional radiomics," Cancers (Basel)., vol. 13, No. 8, 2021, doi: 10.3390/cancers13081814.

Liu Q. et al.: "Predicting EGFR mutation subtypes in lung adenocarcinoma using 18F-FDG PET/CT radiomic features," Transl. Lung Cancer Res., vol. 9, No. 3, pp. 549-562, 2020, doi: 10.21037/tlcr.2020.04.17.

Saltz J. et al.: "Spatial Organization and Molecular Correlation of Tumor-Infiltrating Lymphocytes Using Deep Learning on Pathology Images," Cell Rep., vol. 23, No. 1, pp. 181-193.e7, 2018, doi:10.1016/j.celrep.2018.03.086.

Uijlings J.R. et al., "Selective search for object recognition" Int. J. Comp. Vision, 104(2), 154-171 (2013).

Wang, Chengdi et al: "Deep Learning to Predict EGFR Mutation and PD-LI Expression Status in Non-Small-Cell Lung Cancer on Computed Tomography Images", Journal of Oncology; vol. 2021, Dec. 31, 2021 (Dec. 31, 2021), pp. 1-11, XP55933971.

Wang S. et al.: "Predicting EGFR mutation status in lung adenocarcinoma on computed tomography image using deep learning," Eur. Respir. J., vol. 53, No. 3, 2019, doi: 10.1183/13993003.00986-2018.

Coudray N. et al.: "Classification and mutation prediction from non-small cell lung cancer histopathology images using deep learning," Nat. Med., vol. 24, No. 10, pp. 1559-1567, 2018, doi:10.1038/s41591-018-0177-5.

* cited by examiner

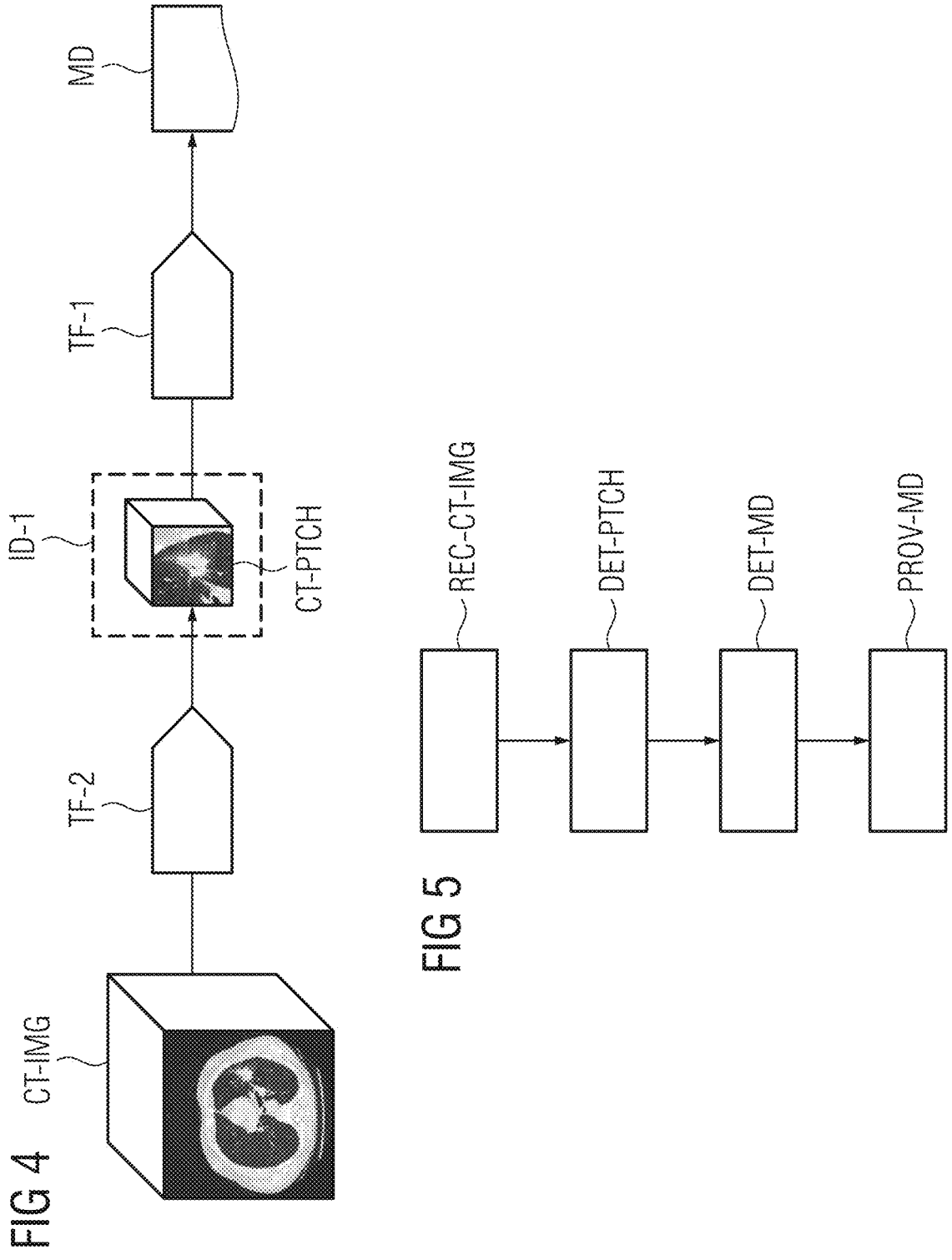

REC-CT-IMG

DET-PTCH

DET-NBD

DET-MD

PROV-MD

FIG 9
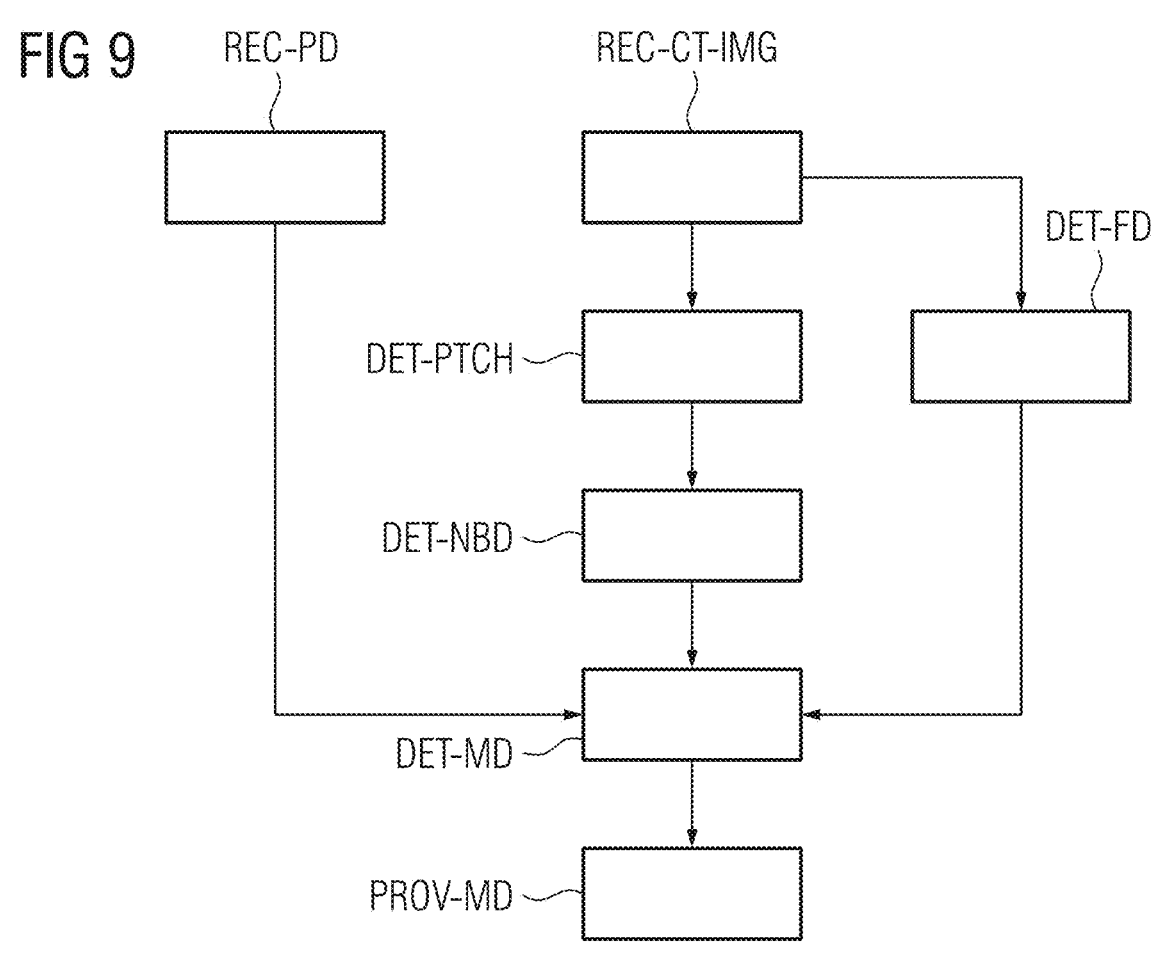
FIG 10
FIG 11
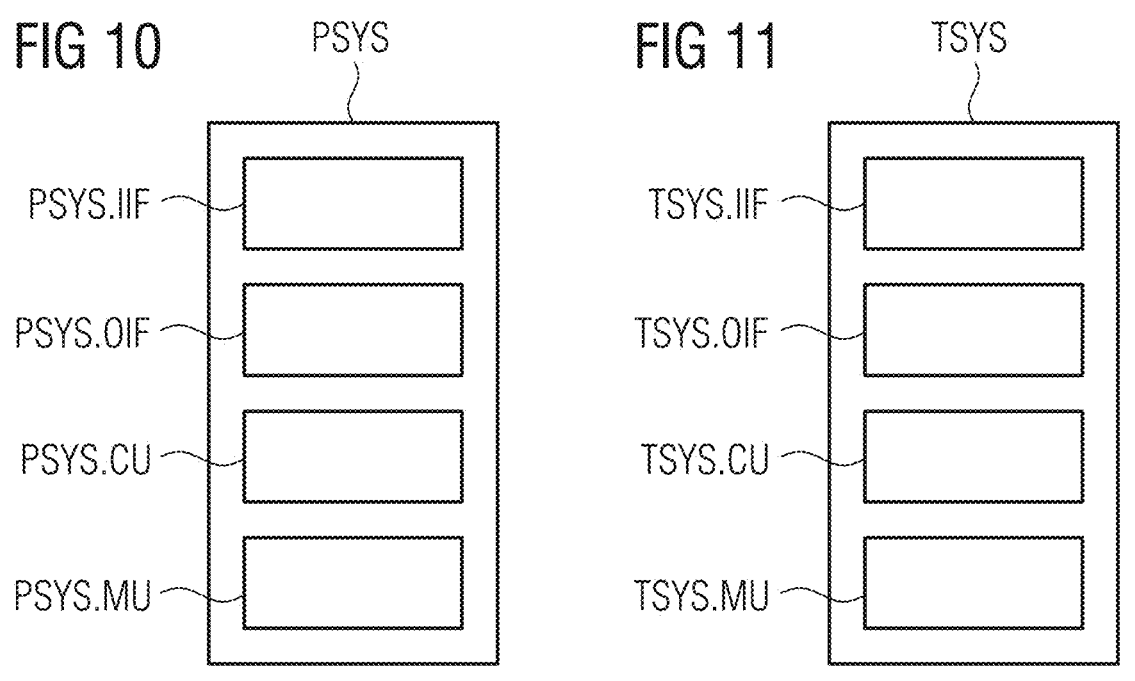

METHODS AND SYSTEMS FOR PROVIDING MOLECULAR DATA BASED ON CT IMAGES

CROSS-REFERENCE TO RELATED APPLICATION(S)

The present application claims priority under 35 U.S.C. § 119 to European Patent Application No. 22152264.2, filed Jan. 19, 2022, the entire contents of which are incorporated herein by reference.

FIELD

In the past decade, advances in personalized medicine have expanded the understanding of underlying biology and molecular mechanisms of several diseases, e.g., lung cancer. As a result, diseases with particular molecular statuses should now be treated with dedicated targeted and chemotherapeutic strategies to improve prognosis.

RELATED ART

For example, programmed death-ligand 1 (an acronym is "PD-L1") and epidermal growth factor receptor (an acronym is "EGFR") mutation are two of the most important molecular information to be assessed for precision medicine in lung cancer. The detection of multiple molecular statuses in patients with lung cancer is crucial to assess the applicability of advanced therapy. Studies showed that therapies targeted against PD-L1 and EGFR mutation improve survival and quality of life compared to conventional chemotherapy. However, molecular testing can be prohibitive, because most lung cancer patients are diagnosed at advanced stage and are unsuitable for invasive sampling procedures. Using molecular testing in screening processes is problematic due to limited laboratory resources and due to high costs.

A known alternative to molecular testing is the analysis of pathology slides for predicting molecular statuses. However, also for an analysis of pathology slides, biopsy or resection samples of lung cancer nodules are required. This invasive procedure is not applicable for most patients with late-stage cancer, and also related with an additional interventional procedure with possible negative outcomes for patients.

SUMMARY

One or more example embodiments of the present invention allow a non-invasive prediction of molecular statuses.

The problem is solved according to the independent claims. Further advantageous embodiments and additional advantageous features are described in the dependent claims and in the specification.

BRIEF DESCRIPTION OF THE DRAWINGS

Properties, features and advantages of one or more example embodiments of the present, as well as the manner they are achieved, are described in the light of the following description and embodiments, which will be described in detail in the context of the drawings. This following description does not limit the invention on the contained embodiments. Same components or parts can be labeled with the same reference signs in different figures. In general, the figures are not for scale.

The numbering and/or order of method steps is intended to facilitate understanding and should not be construed, unless explicitly stated otherwise, or implicitly clear, to mean that the designated steps have to be performed according to the numbering of their reference signs and/or their order within the figures. In particular, several or even all of the method steps may be performed simultaneously, in an overlapping way or sequentially.

Figure 1:
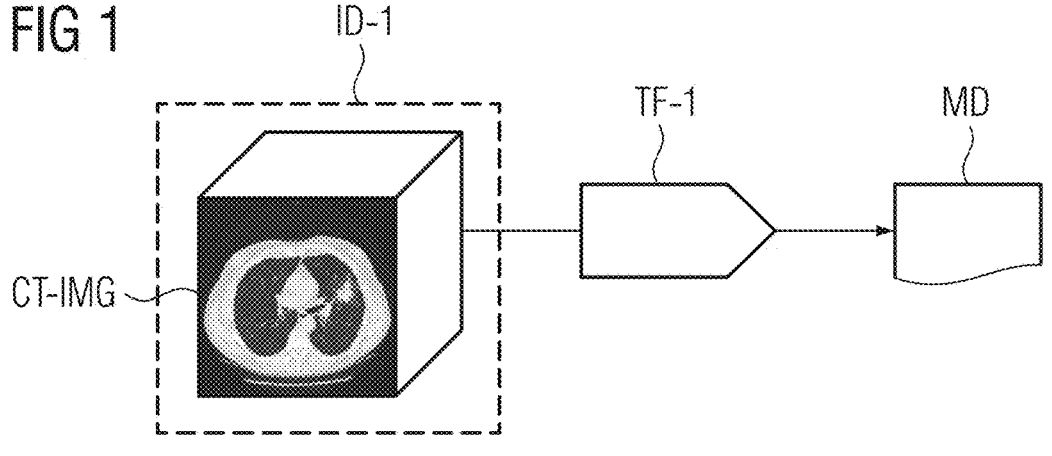
Figure 2:
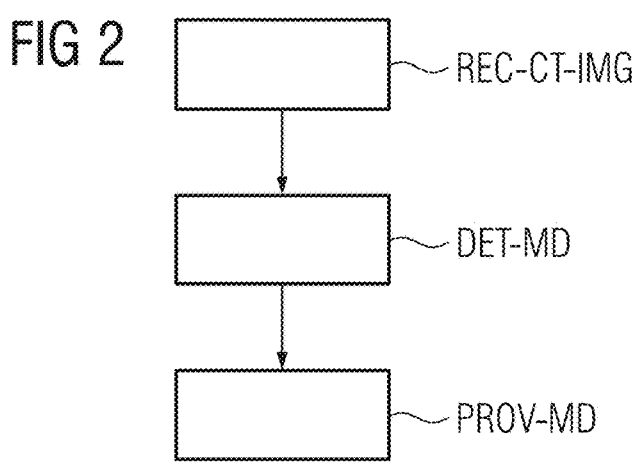
Figure 3:
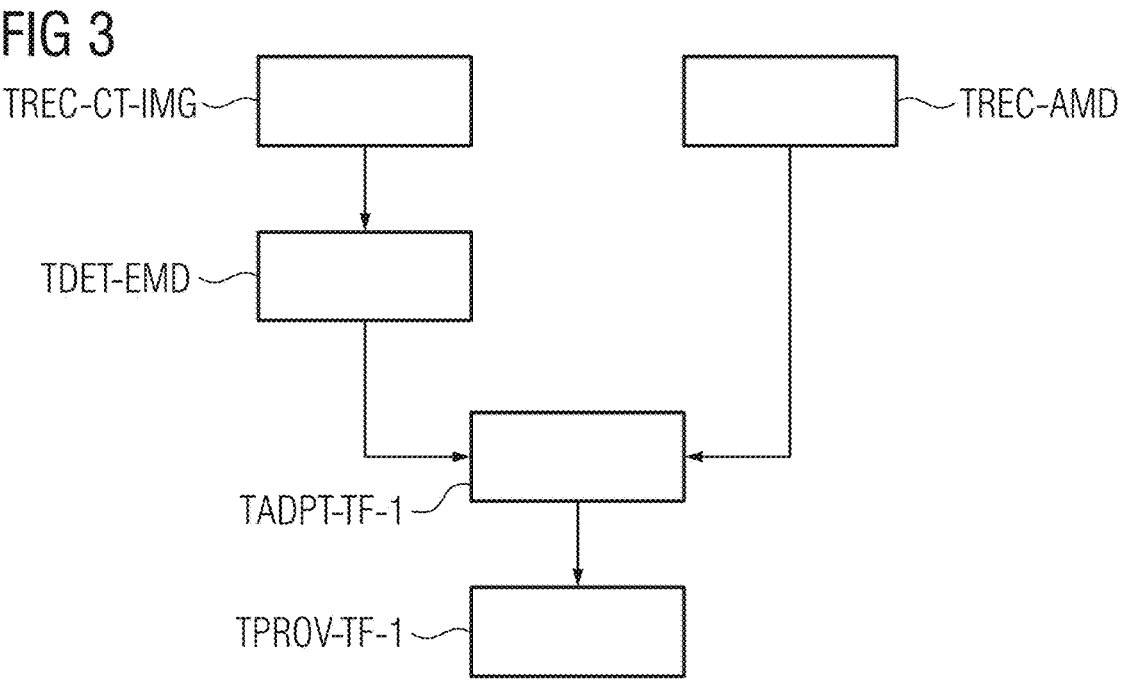
Figure 6:
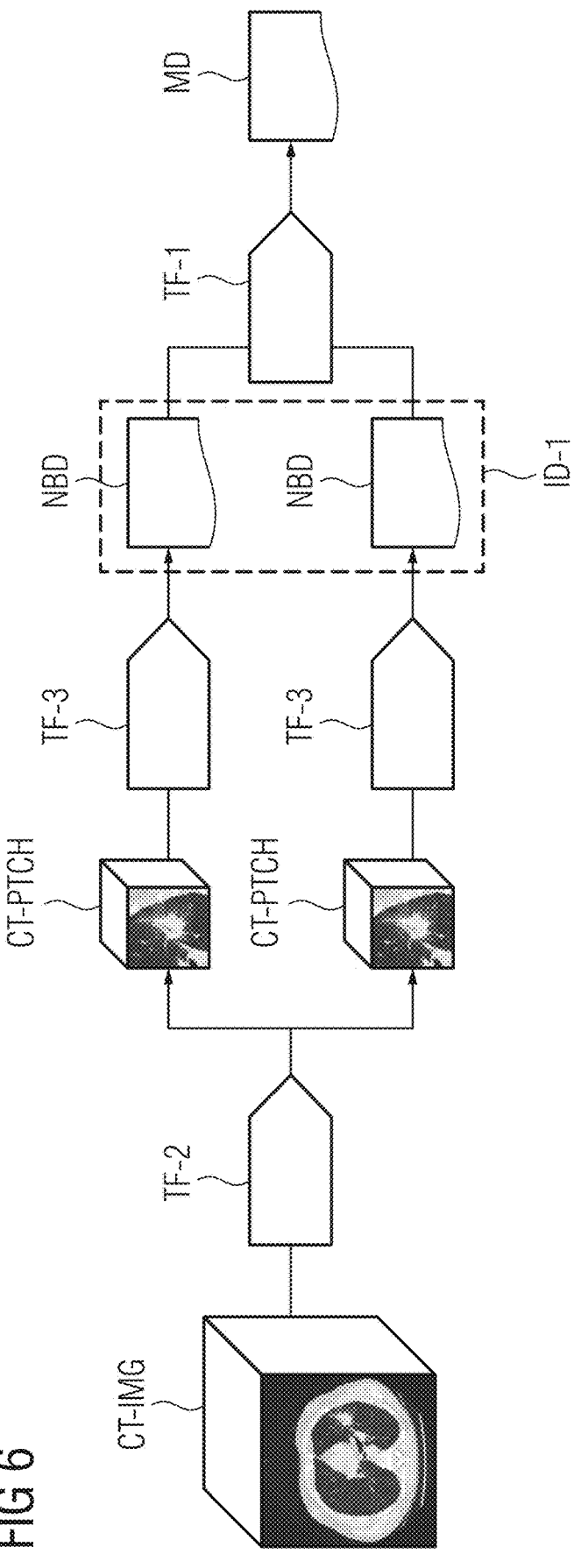
Figure 7:
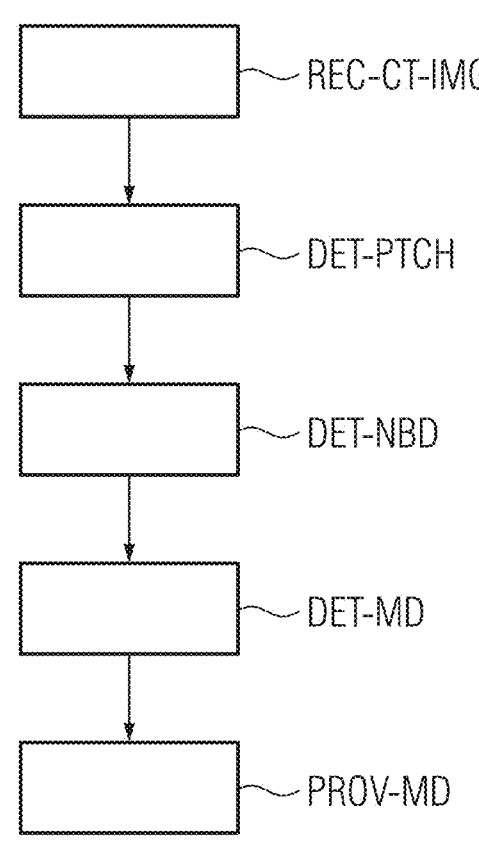
Figure 8:
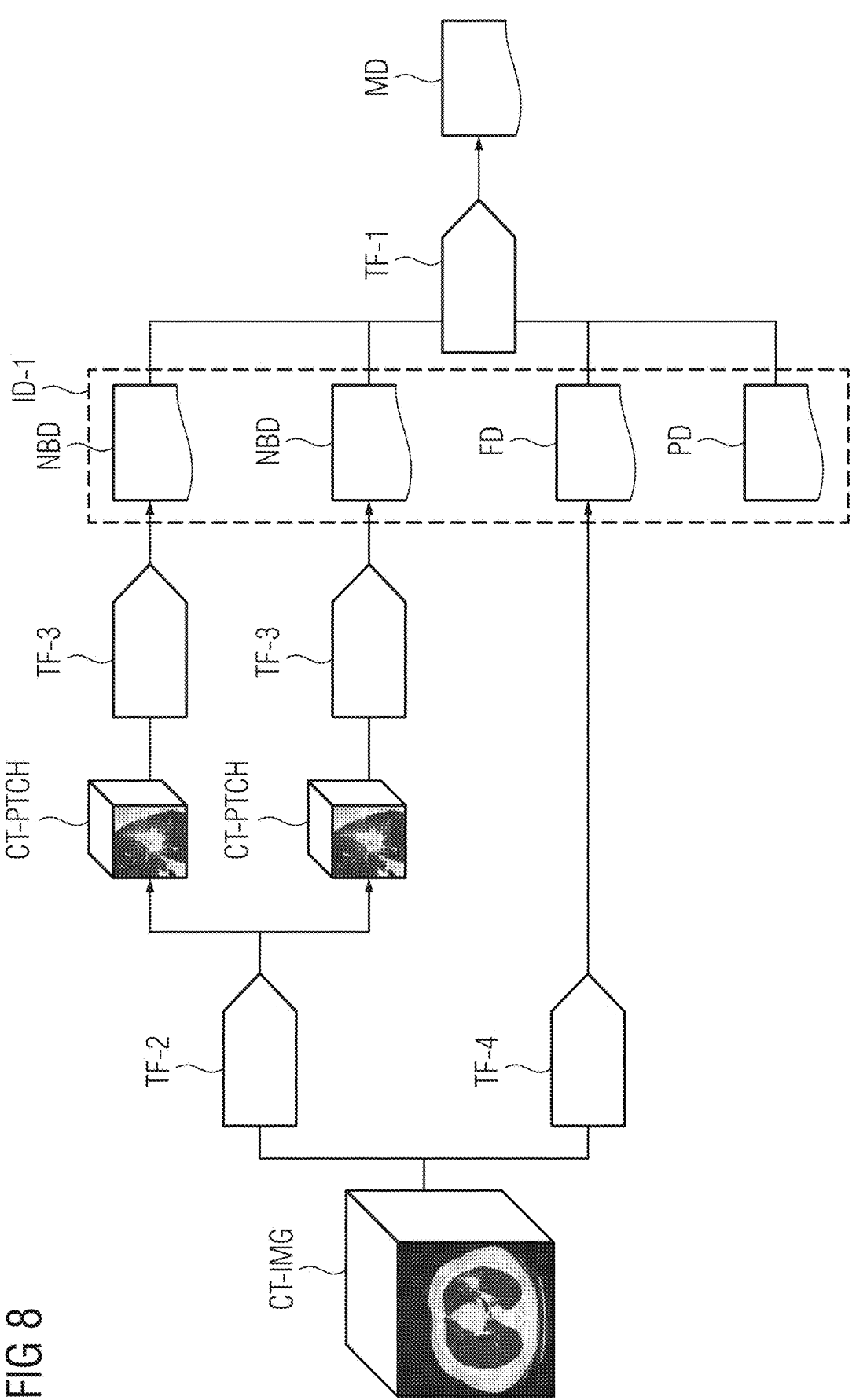

In the following:

FIG. 1 displays a data flow diagram according to a first embodiment of a method for providing molecular data, FIG. 2 displays a flow chart according to the first embodiment of a method for providing molecular data, FIG. 3 displays a flow chart according to the first embodiment of the method for providing a first trained function, FIG. 4 displays a data flow diagram according to a second embodiment of a method for providing molecular data, FIG. 5 displays a flow chart according to the second embodiment of the method for providing a first trained function, FIG. 6 displays a data flow diagram according to a third embodiment of a method for providing molecular data, FIG. 7 displays a flow chart according to the third embodiment of the method for providing a first trained function, FIG. 8 displays a data flow diagram according to a fourth embodiment of a method for providing molecular data, FIG. 9 displays a flow chart according to the fourth embodiment of the method for providing a first trained function, FIG. 10 displays a providing system, and FIG. 11 displays a training system.

DETAILED DESCRIPTION

In the following, one or more example embodiments is described with respect to the claimed systems as well as with respect to the claimed methods. Features, advantages or alternative embodiments herein can be assigned to or implemented within the other corresponding claimed objects and vice versa. In other words, the systems can be improved with features described or claimed in the context of the corresponding method. In this case, the functional features of the methods are executed by the units of the systems.

Furthermore, one or more example embodiments of the present invention is described with respect to methods and systems for providing molecular data as well as with respect to methods and systems for providing trained functions. Features, advantages or alternative embodiments herein can be assigned to or implemented within the other corresponding claimed objects and vice versa. In other words, the trained functions provided can be used within the methods and systems for providing molecular data, and data structures used within methods and systems for providing trained functions can have the same features and advantages as corresponding data structures used in methods and systems for providing molecular data.

In the following, the term "in particular" is used to indicate an optional and/or advantageous additional feature.

One or more example embodiments of the present invention is based on a computer-implemented method for providing molecular data. The method comprises receiving a computed tomography image of at least a part of a lung of a patient, wherein the computed tomography image depicts at least one lung nodule. The molecular data is determined by processing first input data with a first trained function, wherein the first input data is based on the computed tomography image, and wherein the molecular data relates to a biomarker within a genome of the patient, a transcriptome of the patient, a proteome of the patient and/or a metabolome of the patient. Furthermore, the molecular data is provided. Providing the molecular data can comprise displaying, transmitting and/or storing the molecular data.

In particular, the computed tomography image is received by an input interface, in particular, by an input interface of a providing system. In particular, the molecular data is determined by a computation unit, in particular, by a computation unit of the providing system. In particular, the molecular data is provided by an output interface, in particular, by an output interface of the providing system. The input interface and the output interface can be equivalent.

A computed tomography image (an acronym is "CT image") is a medical image acquired by a computed tomography apparatus. In particular, a CT image can be a two-dimensional image (e.g., a single slice of a computed tomography acquisition), a three-dimensional image or a four-dimensional image (e.g., from a time-resolved computed tomography acquisition). In particular, within a four-dimensional image, there are three spatial and one time dimension.

A CT image can comprise a plurality of pixels or voxels, wherein the term "pixel" is mainly used for the building blocks of two-dimensional images, and the term is "voxel" is used for the building blocks of images with arbitrary dimension (mainly for three and more dimensions). However, in the following, the term "voxel" will be used as synonym for the term "pixel or voxel". Each voxel can comprise at least one intensity value corresponding to a certain tissue property (e.g., Hounsfield units corresponding to an X-ray attenuation coefficient).

A CT image can be identical with or encapsulated in one or more DICOM files. Whenever DICOM is mentioned herein, it shall be understood that this refers to the "Digital Imaging and Communications in Medicine" (DICOM) standard, for example according to the current DICOM PS3.1 2020c standard (or any later or earlier version of said standard). It is also possible that several medical images and/or several CT images are encapsulated in a single DICOM file.

In particular, a CT image can comprise additional metadata, e.g., a patient identifier, a patient name, a identifier of the modality used to acquire the CT image, a date and time of the image acquisition, an imaging protocol used during the acquisition of the medical image, and/or other metadate related to the CT image and/or its acquisition process.

In particular, the computed tomography image depicts at least one lobe of the lung of the patient in total. In other words, the computed tomography image is an image of at least one complete lobe of the lung of the patient. In particular, the computed tomography image depicts both lobes of the lung of the patient in total. In other words, the computed tomography image is an image of both complete lobes of the lung of the patient. In particular, the computed tomography image does not depict only a part of the lung of the patient, but the whole lung of the patient.

A lung nodule (a synonym is "pulmonary nodule") is a focal density within the lung of a patient. A lung nodule can represent a benign tumor such as a granuloma or hamartoma, but a lung nodule can also represent a malignant cancer. One or more example embodiments of the present invention can also be applied to lung lesions, so that the term "lung nodule"/"nodule" can be replaced with "lung lesion"/"lesion" in the whole disclosure.

In particular, the computed tomography image depicts a lung nodule, if the computed tomography image is an image of a lung of the patient comprising a lung nodule, and the respective lung nodule is in the field of view and/or region of interest of the computed tomography image.

In particular, molecular data relates to omics-related data of a patient. Herein, omics is a set of different scientific disciplines aiming at the collective characterization and quantification of pools of biological molecules that translate into the structure, function, and dynamics of an organism or organisms, in particular, humans. In particular, omics can denote the scientific disciplines of genomics (related to the genome of a human), epigenomics (related to the epigenome of a human), proteomics (related to the proteome of a human), transcriptomics (related to the transcriptome of a human) and/or metabolomics (related to a metabolome of a human).

In particular, the term "genome" refers to the entirety of the material carriers of the inheritable information (genes) of a cell of an individual, or also to the totality of the inheritable information (genes) of an individual. In particular, biomarkers related to the genome may comprise a base sequence determined by DNA (acronym for "deoxyribonucleic acid") sequencing and/or the probability of occurrence of such a base sequence. In particular, a base sequence comprises a defined sequence of the nucleic bases adenine, guanine, thymine and cytosine.

In particular, the term "epigenome" refers to the entirety of epigenetic states of an individual and consists of a set of chemical changes in the DNA and histone proteins. Such changes can be passed on to the offspring of an organism via transgenerational epigenetic inheritance. In particular, changes in the epigenome can lead to changes in the structure of the chromatin and changes in the function of the genome. The epigenome is particularly involved in the regulation of gene expression, development, tissue differentiation and the suppression of transposable elements. In contrast to the underlying genome, which is largely static in an individual, the epigenome can be dynamically altered, especially by environmental conditions.

In particular, the term "transcriptome" refers to the genes transcribed in a cell at a particular time, i.e. genes transcribed from DNA into RNA (acronym for "ribonucleic acid"), i.e. the entirety of all RNA molecules produced in a cell. In particular, the determination of a transcriptome can be based on the RT-PCR method (acronym for "reverse transcriptase polymerase chain reaction") with degenerate primers, followed by a DNA microarray or DNA sequencing in high throughput ("RNASeq" or "whole transcriptome shotgun sequencing"). An alternative possibility is the serial analysis of gene expression (acronym "SAGE") and its further development SuperSAGE.

In particular, the term "proteome" refers to the entirety of all proteins in a living being, a tissue, a cell and/or a cell compartment, in particular under precisely defined conditions and/or at a specific point in time. In this context, in particular, the proteome can be understood as a state of equilibrium of synthesis and degradation of proteins, and is constantly subject to changes in its composition. These changes are controlled by complex regulatory processes in the course of spatiotemporal gene expression and are significantly influenced by environmental stimuli, diseases, active substances and drugs. Various methods are known for the separation (e.g., serial extraction, serial precipitation, chromatography and/or electrophoresis) and identification or characterization (e.g., mass spectrometry, NMR spectroscopy, protein sequencing by Edman degradation, staining with antibodies or other selective ligands, direct or coupled enzymatic detection and/or phenotypic detection) of individual protein species in the proteome.

In particular, the term "metabolome" refers to the entirety of all characteristic metabolic properties of a cell, tissue or organism. In particular, the metabolome may include the flow rates (=turnover rates), metabolite levels and enzyme activities of the individual metabolic pathways, the interactions between the different metabolic pathways and/or the compartmentalization of the different metabolic pathways within the cells. In particular, the term "lipidome" refers to the complete lipid profile within a cell, tissue, organism, or ecosystem and is a subset of the metabolome.

In particular, a biomarker (a synonym is "biological marker") is a measurable indicator of some biological state or condition within a human.

For example, a biomarker can relate to measurable DNA and/or RNA characteristic that is an indicator of normal biologic processes, pathogenic processes, and/or response to therapeutic or other interventions. A biomarker can be a measurement of the expression of a gene, the function of a gene or the regulation of a gene.

In particular, DNA characteristics can include, but are not limited to single nucleotide polymorphisms (an acronym is "SNP"), Variability of short sequence repeats, Haplotypes, DNA modifications (e.g., methylation), deletions or insertions of a single nucleotide or several nucleotides, copy number variations and/or cytogenetic rearrangements (e.g., translocations, duplications, deletions or inversions). In particular, RNA characteristics can include, but are not limited to RNA sequences, RNA expression levels, RNA processing (e.g., splicing and editing) and/or microRNA levels.

In general, a trained function mimics cognitive functions that humans associate with other human minds. In particular, by training based on training data the trained function is able to adapt to new circumstances and to detect and extrapolate patterns.

In general, parameters of a trained function can be adapted via training. In particular, super-vised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Qlearning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

The first input data of the first trained function is based on the computed tomography image by the first input data comprising the computed tomography image and/or by the first input data comprising the result of at least one preprocessing function applied to the computed tomography image. In particular, the at least one preprocessing function can be a composition of several functions, e.g., other trained functions.

The inventors recognized that based on the proposed method molecular data can be determined based on a computed tomography image without the necessity for doing a dedicated molecular test. A computed tomography exam is both less expensive and faster than a dedicated molecular test. In particular, this implies that the proposed method can be applied to more patients than a dedicated molecular test, and the imaging-based assessment can be used as a pre-test for a dedicated molecular test, wherein the dedicated molecular test is only applied under certain circumstances.

According to one or more example embodiments of the present invention, the method furthermore comprises determining a nodule patch by processing the computed tomography image, advantageously with a second trained function configured to localize lung nodules depicted in computed tomography images, wherein the first input data is based on the nodule patch. In particular, such a second trained function is configured to localize nodules that are likely to be malignant. In particular, the nodule patch is determined by the computation unit, in particular, by the computation unit of the providing system.

In particular, the nodule patch depicts one of the at least one lung nodules depicted by the computed tomography image. In particular, within the step determining a plurality of nodule patches can be determined, each of the plurality of nodule patches depicting one of the at least on lung nodules depicted by the computed tomography image.

In particular, the first input data can be based on the nodule patch by comprising the nodule patch, and/or the first input data can be based on the nodule patch by comprising the result of at least one first preprocessing function applied to the nodule patch. In both cases, the input data can comprise additional data, for example, the first input data can comprise the computed tomography image and/or the result of at least one second preprocessing function applied to the computed tomography image.

In particular, a nodule patch is a part of the computed tomography image comprising less voxel that the computed tomography image. In particular, a nodule patch depicts exactly one lung nodule. In other words, a nodule patch is a proper subset of the computed tomography image. In particular, the nodule patch can be irregularly formed (e.g., comprise voxels corresponding to a segmentation mask of the respective lung nodule), an orthotope (e.g., a rectangle of pixels for two-dimensional computed tomography images, or a rectangular cuboid of voxels for three-dimensional computed tomography images) or an n-cube (e.g., a quadrat of pixels for two-dimensional computed tomography images, or a cube of voxels for three-dimensional computed tomography images). The size of the nodule patch can be pre-defined, or can be determined by the second trained function.

In particular, if the computed tomography image is a two-dimensional image, also the nodule patch is a two-dimensional proper subset of the computed tomography image and/or a two-dimensional image. In particular, if the computed tomography image is a three-dimensional image, the nodule patch is a two-dimensional or three-dimensional subset of the compute tomography image and/or a two-dimensional or three-dimensional image. In particular, if the computed tomography image is a four-dimensional image (three spatial and one time dimension), the nodule patch is a two-dimensional (corresponding to two of the three spatial dimensions), three-dimensional (corresponding to the three spatial dimensions) or four-dimensional (three spatial and one time-dimension) subset of the compute tomography image and/or a two-dimensional (corresponding to two of the three spatial dimensions), three-dimensional (corresponding to the three spatial dimensions) or four-dimensional (three spatial and one time-dimension) image.

In particular, the second trained function can create as output a coordinate tuple referring to a voxel of the computed tomography image that correspond to the center of the probably malignant nodule (or a plurality of coordinate tuples, each of the coordinate tuples refereeing to a voxel of the computed tomography image that corresponds to the center of one of a plurality of probably malignant nodules), and the nodule patch can be orthotope and/or n-cube of pre-defined size centered around the determined coordinate tuple.

The inventors recognized that based on nodule patches the molecular data related to single nodules can be calculated more exactly by the first trained function. In particular, if using pre-defined nodule patch sizes, the first trained function can be directly trained on the image characteristics of nodule patches, so that it is not necessary implement the location of potentially malignant nodules within the first trained function by training.

According to one or more example embodiments of the present invention, the method comprises determining nodule-based data by processing the nodule patch, advantageously with a third trained function (in particular, taking as input a nodule patch and calculating as output nodule-based data), wherein the nodule-based data relates to the biomarker within the genome of the patient, the transcriptome of the patient, the proteome of the patient and/or the metabolome of the patient, wherein the first input data comprises the nodule-based data. In particular, the nodule-based data is determined by the computation unit, in particular, by the computation unit of the providing system.

In the case a plurality of nodule patches is determined, nodule-based data can be determined for each of the nodule patches separately by processing each of the nodule patches separately, advantageously by the same third trained function. In this case, the first input data can comprise all nodule-based data determined, an average of the nodule-based data determined or a selection of one of the nodule-based data determined (e.g., the most extremal nodule-based data determined).

In particular, while in one or more example embodiments of the present invention the first input data comprises nodule-based data, the first input data can also comprise additional data, in particular, the first input data can be based on the computed tomography image and/or on the nodule patch.

The inventors recognized that by using nodule-based data as input for the first trained function this certain aspect of preprocessing does not need to be implemented into the first trained function via training. Furthermore, the influence of the several parts of the first input data on the processing results can be controlled separately to avoid that the first trained function is overfitted to an certain aspect of the computed tomography image.

According to one or more example embodiments of the present invention, the nodule-based data relates to an expression of programmed death-ligand 1 (acronym "PD-L1") within the proteome of the patient and/or to an mutation of epidermal growth factor receptor, (acronym "EGFR") within the genome of the patient. In particular, the nodule-based data comprises a level of the expression of PD-L1 within the proteome of the patient and/or a probability of a mutation of EGFR within the genome of the patient, and/or a combined numerical value.

Programmed death-ligand 1, which is also referred to as cluster of differentiation 274 (acronym "CD274") or B7 homolog 1 (acronym "B7-H1") is a protein that in humans is encoded by the CD274 gene. PD-L1 binds to its receptor programmed cell death protein 1 (acronym "PD-1") found on activated T cells, B cells, and myeloid cells, to modulate activation or inhibition. Upregulation of PD-L1 may allow cancers to evade the host immune system. Clinical studies found that high tumor expression of PD-L1 was associated with increased tumor aggressiveness and an increased risk of death. Several PD-L1 inhibitors are in development as immuno-oncology therapies and are showing good results in clinical trials.

Epidermal growth factor receptor a transmembrane protein that is a receptor for members of the epidermal growth factor family (EGF family) of extracellular protein ligands. Mutations in epidermal growth factor receptor (in particular, within the tyrosine kinase domain) can be associated with some types of lung cancers, e.g., lung adenocarcinomas. Those mutations can be identified and targeted with EGFR-tyrosine kinase inhibitors (acronym TKI) and can lead to an improvement of the therapy of those lung cancers.

The inventors recognized that by the nodule-based data relating to an expression of PD-L1 and/or to a mutation of EGFR significant molecular biomarkers can be predicted based on computed tomography images. Furthermore, the inventors recognized that these two molecular biomarkers can be predicted with a high accuracy from computed tomography images.

According to one or more example embodiments of the present invention, the method comprises determining feature data by processing the computed tomography image with a fourth trained function, wherein the first input data comprises the feature data. In particular, the feature data is determined by the computation unit, in particular, by the computation unit of the providing system.

In particular, the feature data relates to an imaging biomarker, or is identical to an imaging biomarker. An imaging biomarker is a feature of an image relevant to the diagnosis of the patient. In particular, the feature data relates to imaging biomarkers not related to lung nodules. In particular, the feature data can be related to the status of lymph nodes visible in the computed tomography image, the presence of emphysema in the lung of the patient, or the metastasis pattern visible in the computed tomography image.

The inventors recognized that using additional patient characteristics derivable from the complete computed tomography image improves the accuracy of the prediction of molecular data, compared to only relying on nodule patches. Furthermore, the inventors recognized that trained functions are advantageous for extracting those additional patient characteristics from computed tomography images.

According to one or more example embodiments of the present invention, the method comprises receiving patient data related to the patient, the patient data comprising non-imaging-based data. According to this aspect the first input data comprises the patient data.

In particular, the non-imaging-based data comprises the age of the patient, the sex of the patient, the smoking history of the patient, laboratory values related to the patient, and/or comorbidities of the patient.

The inventors recognized that using additional patient data not derivable from the computed tomography image improves the accuracy of the prediction of molecular data, compared to only relying on nodule patches.

According to one or more example embodiments of the present invention, the patient data comprises at least one of: a status of at least one lymph node of the patient, a presence of pulmonary emphysema within the patient, a metastasis pattern related to the patient, an age of the patient, a muscle and fat distribution of the patient, and/or a smoking history of the patient.

The inventors recognized that said elements of patient data are good predictors for cancer-related questions, and that using said elements improves the accuracy of the prediction of molecular data, compared to only relying on nodule patches and compared to using other patient data.

According to a further aspect the first trained function consists of at least one fully connected layer, or comprises a convolutional neural network. In particular, this implies that the first trained function is or comprises a neural network. In particular, if the first input data comprises the computed tomography image, the first trained function comprises a convolutional neural network. In contrast, if the first input data does comprise nodule-based data and does not comprise the computed tomography image, the first trained function consists of at least one fully connected layer.

A fully connected layer in a neural network is a layer where all the input nodes are connected to every output node. In other words, the fully connected layer multiplies the input by a weight matrix and potentially adds a bias vector, wherein the entries of the weight matrix are the parameters or weights that are adapted by training.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

The inventors recognized that by using at least one fully connected layers different components of the first input data can be efficiently processed and summarized to a meaningful data predictive of the molecular status. The inventors furthermore recognized that by the first trained function comprising a convolutional neural network images in the first input data can be processed in a very efficient way, and that relevant features can be extracted from images in the first input data implying a better prediction of the molecular status.

According to one or more example embodiments of the present invention, the second trained function is a region-based convolutional neural network, and/or the third trained function is a convolutional neural network, and/or the fourth trained function is a convolutional neural network.

A region-based convolutional neural network (acronym "R-CNN") takes as input an image of arbitrary dimension (e.g., the computed tomography image) and creates as an output at least one bounding box, and advantageously also a category corresponding to each of the at least one bounding boxes. R-CNNs were introduced in the document R. Girshick et al., "Rich feature hierarchies for accurate object detection and semantic segmentation", https://arxiv.org/abs/1311.2524 (2013).

In particular, using a standard R-CNN comprises creating a set of regions of interest (acronym "ROI"), e.g., based on a selective search algorithm, wherein in most cases orthotope-like regions of interest are used, and wherein the ROI defines a bounding box for a possible object to be detected. Furthermore, it comprises processing each of the set of ROIs with a convolutional neural network to calculate a feature set related to the ROIs (if in the previous step ROIs of different size are created, the ROIs can be warped to a constant size). Furthermore, it comprises applying a classification algorithm (e.g., a support vector machine or a neural network) to the feature sets calculated to classify the content of each ROI.

Instead of standard R-CNNs, improved methods like "Fast R-CNN" (where the convolutional neural network is only used once at the whole input image, and the feature output of the CNN is transferred to the respective ROIs based on a certain pooling operation denoted as "ROIPooling"), "Faster R-CNN" (wherein the creation of the ROIs is directly performed by the convolutional neural network) and/or "Mask R-CNN" (where a segmentation of the detected objects is included) can be used.

The inventors recognized that by choosing a R-CNN as second trained function nodule patches that correspond to a potential lesion can be extracted in a reliable and accurate way. Furthermore, by using a CNN for the third and/or the fourth trained function, the respective inputs can be processed based on hierarchical patterns without large number of weights, so that the computational efficiency is increased, and the risk of overfitting is decreased.

According to one or more example embodiments of the present invention, the molecular data relates to a biomarker within the genome of the patient, the transcriptome of the patient, the proteome of the patient and/or the metabolome of the patient by comprising a numerical value, the numerical value indicating the probability of the presence of the biomarker within the genome of the patient, the transcriptome of the patient, the proteome of the patient and/or the metabolome of the patient and/or the level of the biomarker within the genome of the patient, the transcriptome of the patient, the proteome of the patient and/or the metabolome of the patient. Another term for "probability" is "likelihood".

In particular, the probability of a biomarker relates to how likely a certain biomarker is present within the genome of the patient, the transcriptome of the patient, the proteome of the patient and/or the metabolome of the patient. In particular, the level of a biomarker relates to a ratio or a percentage of cells in a tumor or a biopsy sample that exhibit the biomarker within the genome, the transcriptome, the proteome and/or the metabolome.

The inventors recognized that in most cases based on imaging data it is not possible to make an absolutely certain statement about the presence of a biomarker (which is only possible by performing molecular tests, e.g., doing a genomic sequencing). However, it is possible to derive a certain probability for the presence of a biomarker from the imaging data, which can then be used for selecting cases for the actual molecular test and increasing the pre-test probability for such molecular tests.

According to one or more example embodiments of the present invention, the molecular data relates to an expression of programmed death-ligand 1 within the proteome of the patient and/or to a mutation of epidermal growth factor receptor within the genome of the patient. In particular, the molecular data comprises the level of the expression of PD-L1 within the proteome of the patient and/or to the probability for a mutation of EGFR within the genome of the patient.

The inventors recognized that by the molecular data relating to an expression of PD-L1 and/or to a mutation of EGFR significant molecular biomarkers can be predicted based on computed tomography images. Furthermore, the inventors recognized that these two molecular biomarkers can be predicted with a high accuracy from computed tomography images. Furthermore, by the molecular data comprising the level of the expression of PD-L1 within the proteome of the patient and/or to the probability for a mutation of EGFR within the genome of the patient, cases for the actual molecular tests can be selected and the pre-test probability for such molecular tests can be increased.

One or more example embodiments of the present invention is furthermore based on a computer-implemented method for providing a first trained function. The method comprises receiving a computed tomography image of at least a part of a lung of a patient, wherein the computed tomography image depicts at least one lung nodule. The method furthermore comprises determining estimated molecular data by processing first input data with a first trained function, wherein the first input data is based on the computed tomography image. The method furthermore comprises receiving actual molecular data of the patient, wherein the actual molecular data relates to a biomarker within a genome of the patient, a transcriptome of the patient, a proteome of the patient and/or a metabolome of the patient. The method furthermore comprises adapting at least one parameter of the first trained function based on a comparison of the actual molecular data and the estimated molecular data. The method furthermore comprises providing the first trained function. Providing the first trained function can comprise displaying, transmitting and/or storing the trained function. In particular, the provided first trained function can be used within the method of providing molecular data according to one or more example embodiments of the present invention.

In particular, the computed tomography image is received by an input interface, in particular, by an input interface of a training system. In particular, the estimated molecular data is determined by a computation unit, in particular, by a computation unit of the training system. In particular, the actual molecular data is received by the input interface, in particular, by the input interface of the training system. In particular, the at least one parameter of the first trained function is adapted by the computation unit, in particular, by the computation unit of the training system. In particular, the molecular data is provided by an output interface, in particular, by an output interface of the training system. The input interface and the output interface can be equivalent.

In particular, adapting at least one parameter of the first trained function based on a comparison of the actual molecular data and the estimated molecular data can be based on the difference or a norm of the difference of the actual molecular data and the estimated molecular data. In particular, if the first trained function is a neural network or comprises a neural network, the parameters adapted can be the edge weights of the neural network, and adapting the edge weights can be based on the backpropagation algorithm.

In particular, the computed tomography image, the first input data and the first trained function can comprise all advantageous aspects and embodiments as described with respect to the same objects in the context of the method for providing molecular data. Furthermore, the estimated molecular data and the actual molecular data can comprise all advantageous aspects and embodiments as described with respect to the molecular data in context of the method for providing molecular data. Furthermore, for determining the estimates molecular data, the method for providing the first trained function can be extended by additional steps described with respect to aspects of the method for providing molecular data.

The inventors recognized that based on the proposed training steps a first trained function can be provided that is suitable for use in the method for providing molecular data according to one or more example embodiments of the present invention, and that by using said first trained function the said method for providing molecular data gives reliable and good results.

One or more example embodiments of the present invention is furthermore based on a providing system for providing molecular data, comprising means for receiving a computed tomography image of at least a part of a lung of a patient, wherein the computed tomography image depicts at least one lung nodule, means for determining the molecular data by processing first input data with a first trained function, wherein the first input data is based on the computed tomography image, wherein the molecular data relates to a biomarker within a genome of the patient, a transcriptome of the patient, a proteome of the patient and/or a metabolome of the patient, means for providing the molecular data.

One or more example embodiments of the present invention is furthermore based on a providing system for providing molecular data, comprising a calculation unit, an input interface and an output interface, the providing system being configured for:

receiving a computed tomography image of at least a part of a lung of a patient, wherein the computed tomography image depicts at least one lung nodule, determining the molecular data by processing first input data with a first trained function, wherein the first input data is based on the computed tomography image, wherein the molecular data relates to a biomarker within a genome of the patient, a transcriptome of the patient, a proteome of the patient and/or a metabolome of the patient, providing the molecular data.

In particular, the providing system is configured for receiving the computed tomography image by its input interface being configured for receiving the computed tomography image. In particular, the providing system is configured for determining the molecular data by its calculation unit being configured for determining the molecular data. In particular, the providing system is configured for providing the molecular data by its output interface being configured for providing the molecular data. In particular, the input interface and the output interface can be the same entity, or the input interface and the output interface can be different entities.

In particular, the providing systems can be configured to execute the method for providing the molecular according to one or more example embodiments of the present invention. The providing systems are configured to execute the method and its aspects by its input interface, its calculation unit and its output interface being configured to execute the respective method steps.

One or more example embodiments of the present invention is furthermore based on a computer program product comprising instructions which, when the program is executed by a computer, cause the computer to carry out the method of providing molecular data or the method for providing a trained function according to one or more example embodiments of the present invention.

One or more example embodiments of the present invention is furthermore based on a computer-readable storage medium comprising instructions which, when executed by a computer, cause the computer to carry out the method of providing molecular data or the method for providing a trained function according to one or more example embodiments of the present invention.

The realization of one or more example embodiments of the present invention by a computer program product and/or a computer-readable medium has the advantage that already existing servers, devices and clients can be easily adapted by software updates in order to work as proposed.

The said computer program products can be, for example, a computer program or comprise another element apart from the computer program. This other element can be hardware, for example a memory device, on which the computer program is stored, a hardware key for using the computer program and the like, and/or software, for example a documentation or a software key for using the computer program.

FIG. 1 displays a data flow diagram according to a first embodiment of a method for providing molecular data MD, and FIG. 2 displays a flow chart according to the first embodiment of the method for providing molecular data.

In this first embodiment, a computed tomography image CT-IMG is used as input for a first trained function TF-1, and the molecular data MD is the output of the first trained function TF-1.

In this first embodiment, the computed tomography image CT-IMG is a three-dimensional image in the DICOM format. In particular, the computed tomography image CT-IMG comprises 512×512×512 voxel, wherein each of the voxels comprises an intensity values in Houndsfield units, corresponding to an X-ray attenuation coefficient of the tissue imaged by the respective voxel. It is also possible to use other formats of the computed tomography image CT-IMG, and/or to preprocess the computed tomography image CT-IMG. The computed tomography image CT-IMG of at least a part of a lung of a patient, and the computed tomography image CT-IMG depicts at least one lung nodule within a lung of the patient.

In this first embodiment, the molecular data MD comprises two numerical values, the first numerical value corresponds to the level of expression of programmed death-ligand 1, PD-L1, within the proteome of the patient, and the second numerical value corresponds to the probability of a mutation of epidermal growth factor receptor, EGFR, within the genome of the patient. In particular, the numerical values can be arranged within a vector.

In the first embodiment, the first trained function TF1 is a convolutional neural network, in particular, a deep convolutional neural network. The first trained function TF-1 comprises convolutional layers, pooling layers and fully connected layers. Table A lists an example structure for a first trained function TF-1 being a convolutional neural network configured to be used in the first embodiment.

TABLE A

Structure of first trained function TF-1
(convolutional neural network) in first embodiment

| A.1 | Input layer → |
| | 512 × 512 × 512 × 1 |
| A.2 | Conv. layer (K: 5 × 5 × 5 kernel, P: 2, F: 2) → |
| | 512 × 512 × 512 × 2 |
| A.3 | Pool. layer (4 × 4 × 4 averaging) → |
| | 128 × 128 × 128 × 2 |
| A.4 | Conv. layer (K: 5 × 5 × 5 kernel, P: 2, F: 2) → |
| | 128 × 128 × 128 × 4 |
| A.5 | Pool. layer (4 × 4 × 4 averaging) → 32 × 32 × 32 × 4 |
| A.6 | Conv. layer (K: 5 × 5 × 5 kernel, P: 2, F: 1) → |
| | 32 × 32 × 32 × 4 |
| A.7 | Pool. layer (4 × 4 × 4 averaging) → 8 × 8 × 8 × 4 |
| A.8 | Conv. layer (K: 5 × 5 × 5 kernel, P: 2, F: 2) → |
| | 8 × 8 × 8 × 8 |
| A.9 | Pool. layer (2 × 2 × 2 max. pool) → 4 × 4 × 4 × 8 |
| A.10 | Flatten: → 512 |
| A.11 | Fully connected → 120 |
| A.12 | Fully connected → 20 |
| A.13 | Fully connected → 2 |

In the input layer (line A.1), there is one node for each voxel of the computed tomography image CT-IMG, each voxel having one channel (the respective intensity value). After the input, there are four convolutional layers (line A.2, A.4, A.6 and A.8), each of the four convolutional layers followed by a pooling layer (lines A.3, A.5, A.7 and A.9). For each of the convolutional layers, a 5×5×5 kernel is used (indicated by "K: 5×5×5") with a padding of 2 (indicated by "P: 2") and either one or two filters/convolutional kernels (indicated by "F: 1" or "F: 2"). Furthermore, there are four pooling layers (line A.3, A.5, A.7 and A.9), the first three layers implementing an averaging operation over patches of size 4×4×4, and the last pooling layer implementing an maximum operation over patches of size 2×2×2. The last layers of the network are three fully connected layers with 120 nodes (line A.11), 20 nodes (line A.12) and 2 nodes (line A.13), wherein the last layer also corresponds to the output layer. The first node of the output layer corresponds to the level of expression of programmed death-ligand 1, PD-L1, within the proteome of the patient, and the second node of the output layer corresponds to the probability of a mutation of epidermal growth factor receptor, EGFR, within the genome of the patient.

As displayed in FIG. 2, the first embodiment of the method for providing molecular data comprises as first step receiving REC-CT-IMG the computed tomography image CT-IMG, in particular by an input interface PSYS.IIF. The second step is determining DET-MD the molecular data MD by processing first input data ID-1 with a first trained function TF-1. In this first embodiment, the first input data ID-1 is equivalent with the computed tomography image CT-IMG, and the molecular data MD comprises two numerical values as stated above. In particular, the step of determining DET-MD the molecular data is executed by an computation unit PSYS.CU. The last step of the first embodiment is providing PROV-MD the molecular data MD. In particular, the step of providing PROV-MD the molecular data MD is executed by an output interface PSYS.OIF and comprises storing, displaying and/or transmitting the molecular data MD.

FIG. 3 displays a flow chart according to the first embodiment of the method for providing a first trained function TF-1. The first trained function TF-1 can be used in the first embodiment of the method for providing molecular data MD as described with respect to FIG. 2.

The first step of the displayed embodiment is receiving TREC-CT-IMG a computed tomography image CT-IMG. The computed tomography image CT-IMG has the same characteristics and properties as described with respect to the first embodiment of the method for providing molecular data MD as described with respect to FIG. 1 and FIG. 2.

Another step of the displayed embodiment is determining TDET-EMD estimated molecular data by processing first input data ID-1 with a first trained function TF-1. In this embodiment, the first input data ID-1 is equivalent to the computed tomography image CT-IMG. The estimated molecular data EMD has the same structure as the molecular data MD as described with respect to FIG. 1 and FIG. 2, and the first trained function TF-1 has the same structure as described with respect to FIG. 1, FIG. 2 and Table A.

A further step of the displayed embodiment is receiving TREC-AMD actual molecular data of the patient. The step of receiving TREC-AMD actual molecular data can be executed before, during or after the steps of receiving TREC-CT-IMG a computed tomography image CT-IMG and/or determining TDET-EMD estimated molecular data. In this embodiment, the actual molecular data is a binary vector with two entries, the two entries being based on molecular tests executed on the patient. The first entry of the vector is 1 if there is an expression of programmed death-ligand 1, PD-L1, within the proteome of the patient, and 0 if there is no such expression. The second entry of the vector is 1 if there is a mutation of epidermal growth factor receptor, EGFR, within the genome of the patient, and 0 if there is no such mutation.

A further step of the displayed embodiment is adapting TADPT-TF-1 at least one parameter of the first trained function TF-1 based on a comparison of the actual molecular data and the estimated molecular data. The at least one parameter of the first trained function TF-1 corresponds to a weight of a convolution kernel of the first trained function TF-1 and/or to an edge weight of a fully connected layer within the first trained function TF-1. In this embodiment, the at least one parameter is adapted based on the norm of the (vector-valued) difference of the actual molecular data and the estimated molecular data. In particular, the at least one parameter is adapted by minimizing the cost function (ma−me)2, wherein ma is the two-dimensional vector corresponding to the actual molecular data and me is the two-dimensional vector corresponding to the estimated molecular data. The cost function is minimized by using the backpropagation algorithm.

The last step of the displayed embodiment is providing TPROV-TF-1 the first trained function TF-1. In particular, providing TPROV-TF-1 the first trained function TF-1 can comprise storing or transmitting the first trained function TF1. In particular, the first trained function TF-1 can be used in a method for providing molecular data MD according to one or more example embodiments of the present invention.

The method steps displayed in FIG. 3 describe one or more steps of training for the first trained function TF-1. Advantageously, the training process is performed for at least 1000 iterations based on training sets comprising computed tomography image CT-IMG and corresponding actual molecular data for the same patients.

FIG. 4 displays a data flow diagram according to a second embodiment of a method for providing molecular data MD, and FIG. 5 displays a flow chart according to the second embodiment of the method for providing molecular data.

In this second embodiment, the computed tomography image CT-IMG and the molecular data MD have the same properties and features as described with respect to the first embodiment, FIG. 1 and FIG. 2.

In this embodiment, the second trained function TF-2 is a region-based convolutional neural network, R-CNN that takes as input the computed tomography image CT-IMG and creates as output a coordinate tuple within the computed tomography image CT-IMG that indicates the location of a nodule within the computed tomography image CT-IMG.

The second trained function TF-2 being a region-based R-CNN comprises different elements. The first element is a generator for region proposals, which takes as input the computed tomography image CT-IMG and generates as output a plurality of regions of interest of multiple scales with different shapes (here, different aspect ratios) and sizes within the computed tomography image CT-IMG. In this embodiment, the generator for region proposals is based on the selective search algorithm as described in J. R. Uijlings et al., "Selective search for object recognition" Int. J. Comp. Vision, 104 (2), 154-171 (2013). Alternatively, the generator for region proposals can generate random patches within the computed tomography image CT-IMG. The second element is a pre-trained convolutional neural network being truncated before the output layer, which maps a region of interest to a feature vector (since the pre-trained convolutional neural network takes as an input a region of interest of pre-defined site, the plurality of regions is reshaped to the respective input size before being used as input for the pre-trained convolutional neural network). The third element is a support vector machine that classifieds, based on input feature vectors (being the output of the pre-trained convolutional neural network), whether the input corresponds to a lung nodule. If there is one or more regions of interest with a positive classification result, the center of the region of interest will be the coordinate tuple being the output of the second trained function TF-2.

The nodule patches CT-PTCH are then patches within the computed tomography image CT-IMG having predefined sizes and being centered around the coordinate tuples. In an alternative, the output of the second trained function TF-2 are the regions of interest being classified as comprising a lung nodule. In this case, after determining the nodule patches CT-PTCH, the nodule patches CT-PTCH are resized and/or transformed to a predefined size for the subsequent steps of the method.

In the second embodiment, the first trained function TF-1 is a convolutional neural network, in particular, a deep convolutional neural network, that takes as input the nodule patches CT-PTCH (in this example of size 32×32×32). The first trained function TF-1 comprises convolutional layers, pooling layers and fully connected layers. Table B lists an example structure for a first trained function TF-1 being a convolutional neural network configured to be used in the second embodiment. In this second embodiment, the first input data ID-1 comprises the nodule patch CT-PTCH.

TABLE B

| | Structure of first trained function TF-1 (convolutional neural network) in second embodiment |
|---|---|
| B.1 | Input layer → 32 × 32 × 32 × 1 |
| B.2 | Conv. layer (K: 5 × 5 × 5 kernel, P: 2, F: 4) → 32 × 32 × 32 × 4 |
| B.3 | Pool. layer (2 × 2 × 2 averaging) → 16 × 16 × 16 × 4 |
| B.4 | Conv. layer (K: 3 × 3 × 3 kernel, P: 2, F: 2) → 16 × 16 × 16 × 8 |
| B.5 | Pool. layer (2 × 2 × 2 averaging) → 8 × 8 × 8 × 8 |
| B.6 | Conv. layer (K: 3 × 3 × 3 kernel, P: 2, F: 2) → 8 × 8 × 8 × 16 |
| B.7 | Pool. layer (2 × 2 × 2 averaging) → 4 × 4 × 4 × 16 |
| B.8 | Conv. layer (K: 3 × 3 × 3 kernel, P: 2, F: 2) → 4 × 4 × 4 × 32 |
| B.9 | Pool. layer (2 × 2 × 2 max. pool) → 2 × 2 × 2 × 32 |
| B.10 | Flatten: → 256 |
| B.11 | Fully connected → 120 |
| B.12 | Fully connected → 20 |
| B.13 | Fully connected → 2 |

In the input layer (line B.1), there is one node for each voxel of the nodule patch CT-PTCH, each voxel having one channel (the respective intensity value). After the input, there are four convolutional layers (line B.2, B.4, B.6 and B.8), each of the four convolutional layers followed by a pooling layer (lines B.3, B.5, B.7 and B.9). For the first convolutional layer B.2 a 5×5×5 kernel is used (indicated by "K: 5×5×5"), for the other convolutional layers in lines B.4, B.6 and B.8 a 3×3×3 kernel is used (indicated by "K: 3×3×3"). Each convolutional layer uses a padding of 2 (indicated by "P: 2") and either four or two filters/convolutional kernels (indicated by "F: 4" or "F: 2"). Furthermore, there are four pooling layers (line B.3, B.5, B.7 and B.9), the first three layers implementing an averaging operation over patches of size 2×2×2, and the last pooling layer implementing an maximum operation over patches of size 2×2×2. The last layers of the network are three fully connected layers with 120 nodes (line B.11), 20 nodes (line B.12) and 2 nodes (line B.13), wherein the last layer also corresponds to the output layer. The first node of the output layer corresponds to the level of expression of programmed death-ligand 1, PD-L1, within the proteome of the patient, and the second node of the output layer corresponds to the probability of a mutation of epidermal growth factor receptor, EGFR, within the genome of the patient.

As displayed in FIG. 5, the second embodiment of the method for providing molecular data comprises the steps of the first embodiment as displayed in and described with respect to FIG. 2. Additionally, the method comprises the step of determining DET-PTCH the nodule patch CT-PTCH by processing the computed tomography image CT-IMG with the second trained function TF-2, wherein the second trained function TF-2 is configured to localize lung nodules depicted in computed tomography images CT-IMG. Advantageously, this additional step is executed by the computation unit PSYS.CU.

The training of the first trained function TF-1 within the second embodiment is similar to the training of the first trained function TF-1 within the first embodiment displayed in FIG. 3, with the difference that nodule patches CT-PTCH instead of computed tomography images CT-IMG are used as input for the first trained function TF-1 also in the training phase.

FIG. 6 displays a data flow diagram according to a third embodiment of a method for providing molecular data MD, and FIG. 7 displays a flow chart according to the third embodiment of the method for providing molecular data.

In this third embodiment, the computed tomography image CT-IMG and the molecular data MD have the same properties and features as described with respect to the first embodiment, FIG. 1 and FIG. 2.

In this embodiment, the second trained function TF-2 is a region-based convolutional neural network, R-CNN that takes as input the computed tomography image CT-IMG and creates as output a coordinate tuple within the computed tomography image CT-IMG that indicates the location of a nodule within the computed tomography image CT-IMG. The second trained function TF-2 has the same properties and features as described with respect to the second embodiment, FIG. 4 and FIG. 5.

In this third embodiment, the second trained function TF-2 can identify several nodule patches CT-PTCH within the computed tomography image CT-IMG. Each of the nodule patches CT-PTCH is being used as an input for a third trained function TF-3 being a convolutional network, for generating nodule-based data NBD for each of the nodule patches CT-PTCH. The third trained function TF-3 has the same properties and features as described with respect to the first trained function TF-1 for the second embodiment, FIG. 4 and FIG. 5.

In this embodiment, each of the nodule-based data NBD comprises two numerical values, the first numerical value corresponds to the level of expression of programmed death-ligand 1, PD-L1, within the proteome of the patient, and the second numerical value corresponds to the probability of a mutation of epidermal growth factor receptor, EGFR, within the genome of the patient, wherein the first numerical value and the second numerical value are based only on the respective nodule patch CT-PTCH used as input for the third trained function TF3.

In the third embodiment, the first trained function TF1 is a fully connected neural network. In particular, the first trained function TF-1 can take a predefined number N of nodule-based data NBD as input (so that the first input data ID-1 comprises the nodule-based data NBD), and generates as output the molecular data. The number N should be chosen larger than the usual number of lesions identified in a computer tomography image CT-IMG. If the second trained function TF-2 identifies a number M of lesions that is less than N, then the first M of the N slots for nodule-based data NBD are filled with the respective values of the nodule-based data NBD, and the last N-M of the N slots for nodule-based data NBD are filled with zero values. If by exception the second trained function TF-2 identifies a number M of lesions that is larger than N, then either a random subset of N nodule-based data NBD is used as input for the first trained function TF-1, or the N nodule-based data NBD with the largest sum of squared entries are used as first input data ID-1. Table C lists an example structure for a first trained function TF-1 being a fully connected neural network configured to be used in the third embodiment.

TABLE C

| Structure of first trained function TF-1 (fully-connected neural network) in third embodiment | |
| --- | --- |
| C.1 | Input layer → 40 |
| C.2 | Fully connected layer (ReLU) → 80 |
| C.3 | Fully connected layer (ReLU) → 40 |
| C.4 | Fully connected layer (ReLU) → 20 |
| C.5 | Fully connected layer (ReLU) → 10 |
| C.6 | Fully connected layer (ReLU), Output → 2 |

In the input layer (line C.1), there are two nodes for each nodule-based data NBD, for up to 20 nodule patches CT-PTCH identified by the second trained function TF-2. The first node corresponds to the first numerical value of each nodule-based data, and the second node corresponds to the second numerical value of each nodule-based data NBD. After the input layer, there are four fully connected hidden layers (C.2 to C.5), each of the layers utilizing a rectified linear unit, ReLU, activation function. The layers have 80, 40, 20 and 10 nodes. The output layer is also fully connected layer comprising only two nodes. The first node of the output layer corresponds to the level of expression of programmed death-ligand 1, PD-L1, within the proteome of the patient, and the second node of the output layer corresponds to the probability of a mutation of epidermal growth factor receptor, EGFR, within the genome of the patient.

As displayed in FIG. 7, the third embodiment of the method for providing molecular data comprises the steps of the second embodiment as displayed in and described with respect to FIG. 5. Additionally, the third embodiment comprises the step of determining DET-NBD nodule-based data NBD by processing the nodule patch CT-PTCH with the third trained function TF-3. The first input data ID-1 of the first trained function TF-1 comprises the nodule-based data NBD. Advantageously, this additional step is executed by the computation unit PSYS.CU.

In particular, the step of determining DET-NBD nodule-based data NBD can be executed several times, in particular, the step of determining DET-NBD nodule-based data NBD can be executed once for each of the nodule patches CT-PTCH previously determined.

The training of the first trained function TF-1 within the second embodiment is similar to the training of the first trained function TF-1 within the first embodiment displayed in FIG. 3. However, instead of using first input data ID-1 comprising the computed tomography image CT-IMG, in this third embodiment the first input data ID-1 comprises nodule-based data NBD calculated as described before using the second trained function TF-2 and the third trained function TF-3.

FIG. 8 displays a data flow diagram according to a fourth embodiment of a method for providing molecular data MD, and FIG. 9 displays a flow chart according to the fourth embodiment of the method for providing molecular data.

In this third embodiment, the computed tomography image CT-IMG, the nodule-based data NBD and the molecular data MD, as well as the second trained function TF-2 and the third trained function TF-3 have the same properties and features as described with respect to the previous embodiments.

In this embodiment, the second trained function TF-2 is a region-based convolutional neural network, R-CNN that takes as input the computed tomography image CT-IMG and creates as output a coordinate tuple within the computed tomography image CT-IMG that indicates the location of a nodule within the computed tomography image CT-IMG. The second trained function TF-2 has the same properties and features as described with respect to the second embodiment, FIG. 4 and FIG. 5.

In this fourth embodiment, the computed tomography image CT-IMG is additionally processed by a fourth trained function TF-4 to determined feature data FD. In particular, the fourth trained function TF-4 is a convolutional neural network, in particular, a deep convolutional neural network. The fourth trained function TF-4 comprises convolutional layers, pooling layers and fully connected layers. The fourth trained function TF-4 can have a similar structure as the first trained function TF-1 as described in the first embodiment. In particular, Table A in lines A.1 to A.12 describes a potential structure of the fourth trained function TF-4, wherein in contrast to the first trained function TF-1 within the first embodiment the fourth trained function TF-4 does not contain the last fully connected layer, so that the output layer of the fourth trained function TF-4 comprises 20 nodes. Alternatively, the fourth trained function TF-4 within this fourth embodiment can be equivalent to the first trained function TF1 within the first embodiment.

In this fourth embodiment, the first input data ID-1 of the first trained function TF-1 comprises the nodule-based data NBD, the feature data FD and additional patient data PD. In this fourth embodiment, the patient data PD comprises the following data: a status of at least one lymph node of the patient, a presence of pulmonary emphysema within the patient, a metastasis pattern related to the patient, an age of the patient, a muscle and fat distribution of the patient, and/or a smoking history of the patient.

For using this patient data PD within the first input data ID-1, the different elements of the patient data PD have to be mapped to a number. In particular, each single element of the patient data PD can be mapped to a real number in the interval [0,1]. For the lymph node status, for example a value of 0 can be assigned if the lymph node does not exhibit cancerous structures, a value of 1 can be assigned if the lymph node does exhibit cancerous structures, and a value of 0.5 can be assigned if there is no information about lymph node status (the lymph node status can be assessed based on a sentinel node biopsy). If there are several lymph nodes considered, the value of 1 can be used if there is at least one lymph node exhibiting cancerous structures. For the presence of pulmonary emphysema, for example a value of 1 can be assigned if a pulmonary emphysema is present within the patient, a value of 0 can be assigned if there is no pulmonary emphysema present within the patient, and a value of 0.5 can be assigned if there is no information about the presence of pulmonary emphysema within the patient (the presence of pulmonary emphysema can be assessed based on the computed tomography image CT-IMG by a radiologist, or automatically by a machine learning tool). For the metastasis pattern, for example a value of 1 can be assigned if there are metastasis present in other organs of the patient, a value of 0 can be assigned if there are no metastasis present in other organs of the patient, and a value of 0.5 can be assigned if there is no information on the metastasis pattern (the metastasis pattern can be assessed by physician). For the age of the patient, the age range of 0 to 100 years can be linearly mapped to the interval [0,1]. For the fat and muscle distribution, the ratio of fat weight with respect to the total weight of the patient, and the ration of muscle weight with respect to the total weight of the patient can be used (the values can be measured, for example, based on whole-body air displacement plethysmography). For the smoking pattern, for example a value of 1 can be assigned if the patient has smoked more than a year within the last five years, a value of 0 can be assigned if this is not the case, and a value of 0.5 can be assigned if no information is available.

In the fourth embodiment, the first trained function TF-1 is a fully connected neural network. In particular, the first trained function TF-1 can take a predefined number N of nodule-based data NBD, the feature data and the patient data as input, and generates as output the molecular data MD. For using a varying number of nodule-based data NBD in the first input data ID-1, the same considerations as in the third embodiment are used. Table D lists an example structure for a first trained function TF-1 being a fully connected neural network configured to be used in the fourth embodiment.

TABLE D

| Structure of first trained function TF-1 (fully-connected neural network) in fourth embodiment | |
|---|---|
| D.1 | Input layer → 67 |
| | Thereof: Nodule-based data → 40 |
| | Thereof: Feature data → 20 |
| | Thereof: Patient data → 7 |
| D.2 | Fully connected layer (ReLU) → 100 |
| D.3 | Fully connected layer (ReLU) → 50 |
| D.4 | Fully connected layer (ReLU) → 25 |
| D.5 | Fully connected layer (ReLU) → 12 |
| D.6 | Fully connected layer (ReLU), Output → 2 |

In the input layer (line D.1), there are 67 nodes, wherein the first 40 nodes correspond to nodule-based data NBD (as described with respect to Table C), the following 20 nodes correspond to the feature data (wherein the values of the output nodes of the fourth trained function TF-4 are directly used as input values of these nodes), and the last 7 nodes correspond to the patient data, mapped to intervals of [0,1] as described above (lymph node status, presence of pulmonary emphysema, metastasis pattern, age of the patient, muscle distribution, fat distribution, smoking history). After the input layer, there are four fully connected hidden layers (D.2 to D.5), each of the layers utilizing a rectified linear unit, ReLU, activation function. The layers have 100, 50, 25 and 12 nodes. The output layer is also fully connected layer comprising only two nodes. The first node of the output layer corresponds to the level of expression of programmed death-ligand 1, PD-L1, within the proteome of the patient, and the second node of the output layer corresponds to the probability of a mutation of epidermal growth factor receptor, EGFR, within the genome of the patient.

As displayed in FIG. 9, the fourth embodiment of the method for providing molecular data comprises the steps of the third embodiment as displayed in and described with respect to FIG. 7. Additionally, the fourth embodiment comprises the step of receiving REC-PD patient data PD related to the patient and the step of determining DET-FD feature data FD by processing the computed tomography image CT-IMG with the fourth trained function TF-4. The first input data ID-1 of the first trained function TF-1 comprises the nodule-based data NBD, the feature data FD and the patient data PD. Advantageously, the additional step receiving REC-PD patient data PD is executed by the input interface PSYS.IIF, and the additional step of determining DET-FD feature data FD is executed by the computation unit PSYS.CU.

The training of the first trained function TF-1 within the fourth embodiment is similar to the training of the first trained function TF-1 within the first embodiment displayed in FIG. 3. However, instead of using first input data ID-1 comprising the computed tomography image CT-IMG, in this third embodiment the first input data ID-1 comprises nodule-based data NBD calculated as described before using the second trained function TF-2 and the third trained function TF-3, feature data FD calculated as described before using the fourth trained function TF-4, and patient data FD received.

FIG. 10 displays a providing system PSYS for providing molecular data MD, FIG. 11 displays a training system TSYS for providing a first trained function TF-1.

The providing system PSYS and/or the training system can be a (personal) computer, a workstation, a virtual machine running on host hardware, a microcontroller, or an integrated circuit. In particular, the providing system PSYS and/or the training system TSYS can be mobile devices, e.g., a smartphone or a tablet. As an alternative, the providing system PSYS and/or the training system TSYS can be a real or a virtual group of computers (the technical term for a real group of computers is "cluster", the technical term for a virtual group of computers is "cloud").

The providing system PSYS comprises means for receiving REC-CT-IMG a computed tomography image CT-IMG, said means in the present embodiment comprising an input interface PSYS.IIF. The providing system PSYS furthermore comprises means for determining DET-MD molecular data, said means in the present embodiment comprising a computation unit PSYS.CU. The providing system PSYS furthermore comprises means for providing PROV-MD the molecular data (MD), said means in the present embodiment comprising an output interface PSYS.OIF. The providing system PSYS furthermore comprises a memory unit PSYS.MU.

The training system TSYS comprises means for receiving TREC-CT-IMG a computed tomography image CT-IMG and means for receiving TREC-AMD actual molecular data, said means in the present embodiment comprising an input interface TSYS.IIF. The training system TSYS furthermore comprises means for determining TDET-EMD estimated molecular data and for adapting TADPT-TF-1 at least one parameter of the first trained function TF1, said means in the present embodiment comprising a computation unit TSYS. CU. The training system TSYS furthermore comprises means for providing TPROV-TF-1 the first trained function TF-1, said means in the present embodiment comprising an output interface TSYS. OIF. The training system TSYS furthermore comprises a memory unit TSYS.MU.

An input interface PSYS.IIF, TSYS.IIF and/or an output interface PSYS.IIF, TSYS.IIF can be embodied as a hardware interface or as a software interface (e.g., PCIBus, USB, Firewire, LAN, WiFi, cellular network interface, display). In particular, the input interface PSYS.IIF, TSYS.IIF and/or the output interface PSYS.IIF, TSYS.IIF can be a combination of several other interfaces, in particular, the PSYS.IIF, TSYS.IIF and/or the output interface PSYS.IIF, TSYS.IIF can comprise one or more interfaces as subcomponent.

In particular, the input interface PSYS.IIF, TSYS.IIF and the output interface PSYS.IIF, TSYS.IIF can be the same hardware or software module, so that the respective system PSYS, TSYS only comprises a single integrated interface for input and output.

In general, a computation unit PSYS.CU, TSYS.CU can comprise hardware elements and software elements, for example a microprocessor, a CPU (acronym for "central processing unit"), a GPU (acronym for "graphical processing unit"), a field programmable gate array (an acronym is "FPGA") or an ASIC (acronym for "application-specific integrated circuit"). A CPU, GPU and ASIC may be refered to as processing circuitry. The computation unit PSYS.CU, TSYS.CU can be configured for multithreading, i.e. the computation unit PSYS.CU, TSYS.CU can host different computation processes at the same time, executing the either in parallel or switching between active and passive computation processes. In particular, the computation unit PSYS.CU, TSYS.CU can be a combination of several other computation units, in particular, the computation unit PSYS.CU, TSYS.CU can comprise one or more computation units as subcomponents.

In some example embodiments, the term 'module', 'interface' or the term 'unit' may be replaced with the term 'circuit.' As an example, the computation unit PSYS. CU, TSYS. CU may be part of, or include processor hardware (shared, dedicated, or group) that executes code and memory hardware (shared, dedicated, or group) that stores code executed by the processor hardware.

A memory unit SYS.MU can be e.g. non-permanent main memory (e.g. random access memory) or permanent mass storage (e.g. hard disk, USB stick, SD card, solid state disk).

The providing system PSYS can be configured for executing the method for providing molecular data MD according to one or more example embodiments of the present invention. The training system TSYS can be configured for executing the method for providing a first trained function TF-1 according to one or more example embodiments of the present invention.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments. The present invention may, however, be embodied in many alternate forms and should not be construed as limited to only the embodiments set forth herein.

Further embodiments of the invention are given by the following clauses:

Clause 1: A computer-implemented method for providing a first trained function TF-1, comprising:

receiving TREC-CT-IMG a computed tomography image CT-IMG of at least a part of a lung of a patient, wherein the computed tomography image CT-IMG depicts at least one lung nodule, determining TDET-EMD estimated molecular data by processing first input data ID-1 with a first trained function TF-1, wherein the first input data ID-1 is based on the computed tomography image CT-IMG, receiving TREC-AMD actual molecular data of the patient, wherein the actual molecular data relates to a biomarker within a genome of the patient, a transcriptome of the patient, a proteome of the patient and/or a metabolome of the patient, adapting TADPT-TF-1 at least one parameter of the first trained function TF-1 based on a comparison of the actual molecular data and the estimated molecular data, providing TPROV-TF-1 the first trained function TF-1.

Clause 2: The method according to clause 1, furthermore comprising:

determining a nodule patch CT-PTCH by processing the computed tomography image CT-IMG, advantageously with a second trained function TF-2 configured to localize lung nodules depicted in computed tomography images CT-IMG, wherein the first input data ID-1 is based on the nodule patch.

Clause 3: The method according to clause 2, furthermore comprising:

determining nodule-based data NBD by processing the nodule patch CT-PTCH, advantageously with a third trained TF-3 function, wherein the nodule-based data NBD relates to the biomarker within the genome of the patient, the transcriptome of the patient, the proteome of the patient and/or the metabolome of the patient, wherein the first input data ID-1 comprises the nodule-based data NBD.

Clause 4: The method according to clause 3, wherein the nodule-based data NBD relates to an expression of programmed death-ligand 1, PD-L1, within the proteome of the patient and/or to a mutation of epidermal growth factor receptor, EGFR, within the genome of the patient.

Clause 5: The method according to one of the clauses 2 to 4, furthermore comprising:

determining feature data FD by processing the computed tomography image CT-IMG with a fourth trained function TF-4, wherein the first input data ID-1 comprises the feature data FD.

Clause 6: The method according to one of the preceding claims, furthermore comprising:

receiving patient data PD related to the patient, the patient PD comprising data non-imaging-based data, wherein the first input data ID-1 comprises the patient data.

Clause 7: The method according to clause 6, wherein the patient data (PD) comprises at least one of:

a status of at least one lymph node of the patient, a presence of pulmonary emphysema within the patient, a metastasis pattern related to the patient, an age of the patient, a muscle and fat distribution of the patient, and/or a smoking history of the patient.

Clause 8: The method according to one of the preceding clauses, wherein the first trained function TF-1 is a convolutional neural network or a fully connected layer.

Clause 9: The method according to one of the clauses 2 to 8, wherein the second trained function TF-2 is a region-based convolutional neural network, and/or wherein the third trained function TF-3 is a convolutional neural network, and/or wherein the fourth trained function TF-4 is a convolutional neural network.

Clause 10: The method according to one of the preceding clauses, wherein the molecular data MD relates to a biomarker within the genome of the patient, the transcriptome of the patient, the proteome of the patient and/or the metabolome of the patient by comprising a numerical value, the numerical value indicating the probability of the presence and/or the level of the biomarker within the genome of the patient, the transcriptome of the patient, the proteome of the patient and/or the metabolome of the patient.

Clause 11: The method according to one of the preceding clauses, wherein the molecular data MD relates to an expression of programmed death-ligand 1, PD-L1, within the proteome of the patient and/or to a mutation of epidermal growth factor receptor, EGFR, within the genome of the patient.

Clause 12: A training system TSYS for providing a first trained function TF-1, comprising:

means for receiving TREC-CT-IMG a computed tomography image CT-IMG of at least a part of a lung of a patient, wherein the computed tomography image CT-IMG depicts at least one lung nodule, means for determining TDET-EMD estimated molecular data by processing first input data ID-1 with a first trained function TF-1, wherein the first input data ID-1 is based on the computed tomography image CT-IMG, means for receiving TREC-AMD actual molecular data of the patient, wherein the actual molecular data relates to a biomarker within a genome of the patient, a transcriptome of the patient, a proteome of the patient and/or a metabolome of the patient, means for adapting TADPT-TF-1 at least one parameter of the first trained function TF-1 based on a comparison of the actual molecular data and the estimated molecular data, means for providing TPROV-TF-1 the first trained function TF-1.

Clause 13: A training system TSYS for providing a first trained function TF-1, comprising an input interface TSYS.IIF, an output interface TSYS. OIF and a computation unit TSYS. CU, the training system TSYS configured for:

receiving TREC-CT-IMG a computed tomography image CT-IMG of at least a of a part lung of a patient, wherein the computed tomography image CT-IMG depicts at least one lung nodule, determining TDET-EMD estimated molecular data by processing first input data ID-1 with a first trained function TF-1, wherein the first input data ID-1 is based on the computed tomography image CT-IMG, receiving TREC-AMD actual molecular data of the patient, wherein the actual molecular data relates to a biomarker within a genome of the patient, a transcriptome of the patient, a proteome of the patient and/or a metabolome of the patient, adapting TADPT-TF-1 at least one parameter of the first trained function TF-1 based on a comparison of the actual molecular data and the estimated molecular data, and providing TPROV-TF-1 the first trained function TF-1.

Clause 14: The training system TSYS according to clause 12 or clause 13, furthermore configured to execute the method according to one of the clauses 2 to 11.

The invention claimed is:

1. A computer-implemented method for providing molecular data, the method comprising:

receiving a computed tomography image of at least a part of a lung of a patient, the computed tomography image depicting at least one lung nodule;

determining a nodule patch by processing the computed tomography image with a second trained function, the second trained function configured to localize lung nodules depicted in computed tomography images;

determining nodule-based data by processing the nodule patch with a third trained function, the nodule-based data relating to a biomarker within at least one of a genome of the patient, a transcriptome of the patient, a proteome of the patient, or a metabolome of the patient;

determining feature data by processing the computed tomography image with a fourth trained function, the feature data relating to image biomarkers not related to lung nodules;

determining the molecular data by processing first input data with a first trained function, the first input data including the nodule-based data and the feature data, and the molecular data relating to the biomarker within at least one of the genome of the patient, the transcriptome of the patient, the proteome of the patient, or the metabolome of the patient; and providing the molecular data.

2. The method of claim 1, wherein the nodule-based data relates to at least one of an expression of programmed death-ligand 1 (PD-L1) within the proteome of the patient or a mutation of epidermal growth factor receptor (EGFR) within the genome of the patient.

3. The method of claim 1, further comprising:

receiving patient data related to the patient, the patient data including nonimaging-based data, and the first input data including the patient data.

4. The method of claim 3, wherein the patient data comprises at least one of:

a status of at least one lymph node of the patient, a presence of pulmonary emphysema within the patient, a metastasis pattern related to the patient, an age of the patient, a muscle and fat distribution of the patient, or a smoking history of the patient.

5. The method of claim 1, wherein the first trained function includes at least one fully connected layer, or includes a convolutional neural network.

6. The method of claim 1, wherein at least one of the second trained function is a region-based convolutional neural network, the third trained function is a convolutional neural network, or the fourth trained function is a convolutional neural network.

7. The method of claim 1, wherein the molecular data relates to the biomarker within the at least one of the genome of the patient, the transcriptome of the patient, the proteome of the patient or the metabolome of the patient by comprising a numerical value, the numerical value indicating at least one of a probability of a presence of the biomarker or a level of the biomarker.

8. The method of claim 1, wherein the molecular data relates to at least one of an expression of programmed death-ligand 1 (PD-L1) within the proteome of the patient or to an mutation of epidermal growth factor receptor (EGFR) within the genome of the patient.

9. A computer-implemented method for providing a first trained function, the method comprising:

receiving a computed tomography image of at least a part of a lung of a patient, the computed tomography image depicting at least one lung nodule;

determining a nodule patch by processing the computed tomography image with a second trained function, the second trained function configured to localize lung nodules depicted in computed tomography images;

determining nodule-based data by processing the nodule patch with a third trained function, the nodule-based data relating to a biomarker within at least one of a genome of the patient, a transcriptome of the patient, a proteome of the patient, or a metabolome of the patient;

determining feature data by processing the computed tomography image with a fourth trained function;

determining estimated molecular data by processing first input data with the first trained function, the first input data including the nodule-based data and the feature data;

receiving actual molecular data of the patient, the actual molecular data relating to the biomarker within at least one of the genome of the patient, the transcriptome of the patient, the proteome of the patient, or the metabolome of the patient;

adapting at least one parameter of the first trained function based on a comparison of the actual molecular data and the estimated molecular data; and providing the first trained function.

10. A providing system for providing molecular data, the system comprising:

a memory storing instructions; and processing circuitry configured to execute the instructions to cause the system to, receive a computed tomography image of at least a part of a lung of a patient, the computed tomography image depicting at least one lung nodule, determine a nodule patch by processing the computed tomography image with a second trained function, the second trained function configured to localize lung nodules depicted in computed tomography images;

determine nodule-based data by processing the nodule patch with a third trained function, the nodule-based data relating to a biomarker within at least one of a genome of the patient, a transcriptome of the patient, a proteome of the patient, or a metabolome of the patient;

determine feature data by processing the computed tomography image with a fourth trained function;

determine the molecular data by processing first input data with a first trained function, the first input data including the nodule-based data and the feature data, and the molecular data relating to the biomarker within at least one of the genome of the patient, the transcriptome of the patient, the proteome of the patient, or the metabolome of the patient, and provide the molecular data.

11. A non-transitory computer program product comprising instructions which, when executed by a computer, cause the computer to carry out the method of claim 1.

12. A non-transitory computer-readable storage medium comprising instructions which, when executed by a computer, cause the computer to carry out the method of claim 1.

\* \* \* \* \*